United States Patent
Werner et al.

(10) Patent No.: US 8,330,109 B2
(45) Date of Patent: Dec. 11, 2012

(54) METHOD FOR DETERMINING CONTAMINATION OF MATERIAL USING MID-IR SPECTROSCOPY

(75) Inventors: Gregory James Werner, Puyallup, WA (US); Paul H. Shelley, Lakewood, WA (US)

(73) Assignee: The Boeing Company, Chicago, IL (US)

( * ) Notice: Subject to any disclaimer, the term of this patent is extended or adjusted under 35 U.S.C. 154(b) by 81 days.

(21) Appl. No.: 12/874,545

(22) Filed: Sep. 2, 2010

(65) Prior Publication Data

US 2012/0056082 A1    Mar. 8, 2012

(51) Int. Cl.
*G01N 21/35* (2006.01)
(52) U.S. Cl. .............................. 250/339.09; 250/339.11
(58) Field of Classification Search ............. 250/339.09, 250/339.11
See application file for complete search history.

(56) References Cited

U.S. PATENT DOCUMENTS

| | | | |
|---|---|---|---|
| 5,714,758 A | 2/1998 | Neu | |
| 5,945,676 A * | 8/1999 | Khalil et al. | 250/339.12 |
| 6,031,233 A * | 2/2000 | Levin et al. | 250/339.11 |
| 6,956,228 B2 * | 10/2005 | Shelley et al. | 250/559.4 |
| 7,645,991 B1 | 1/2010 | Shelley et al. | |
| 2003/0232448 A1 | 12/2003 | Shelley et al. | |
| 2004/0099806 A1 | 5/2004 | Shelley et al. | |
| 2010/0032571 A1 | 2/2010 | Shelley et al. | |

OTHER PUBLICATIONS

European Patent Office, "Extended European Search Report," issued in connection with European Application No. 11178792.5, mailed on May 21, 2012, 7 pages.
Hamilton et al. "Grazing-Angle Fiber-Optic IRRAS for in Situ Cleaning Validation," Organic Process Research and Development, American Chemical Society, vol. 9, No. 3, May 1, 2005, pp. 337-343.

* cited by examiner

*Primary Examiner* — Constantine Hannaher
(74) *Attorney, Agent, or Firm* — Hanley, Flight & Zimmerman, LLC (57) ABSTRACT

A method of determining contamination on a material having suspected contamination includes irradiating the material having suspected contamination with infrared energy over a spectrum of wavelengths; detecting the infrared energy reflected from the material having suspected contamination over the spectrum of wavelengths; performing multivariate analysis on the spectrum of the reflected infrared energy; comparing results of the multivariate analysis with a predetermined calibration of infrared energy spectra comprising the spectrum of wavelengths collected from at least one reference material; and determining presence or absence of contamination on the material having suspected contamination based on the predetermined calibration.

20 Claims, 5 Drawing Sheets

FIG. 10

METHOD FOR DETERMINING CONTAMINATION OF MATERIAL USING MID-IR SPECTROSCOPY

TECHNICAL FIELD

The disclosure generally relates to Infrared (IR) measurement methods and apparatus, and more particularly to a method for determining surface contamination of materials including organic surface materials using non-destructive Mid-IR spectroscopy.

BACKGROUND

IR spectroscopy measurements may be useful for a variety of purposes including aerospace, automotive and industrial applications, as well as biological and biomedical applications. For example, infrared (IR) radiation is readily absorbed by materials in association with relative motions (vibrations) of atoms such as carbon, hydrogen, oxygen and nitrogen. As such, IR spectroscopy measurements may indicate a condition of a wide variety of organic as well as inorganic materials.

For example, frequently it is necessary to determine the thickness of a coating material on a substrate, to verify that the film coating thickness is sufficiently thick and/or to verify that the film has the proper composition, including but not limited to, bond primer film thicknesses on a metallic substrate.

IR spectroscopy methods are relatively easy for measurement of contamination on metals, but are difficult for measurement of contamination on dielectric coatings and composite substrates. A conventional method of determining contamination on surface coatings (and composites) may involve performing a hexane extraction of the suspected contaminated area. The hexane solvent and any materials extracted by the solvent may be transferred to a gold cup. After complete evaporation of the solvent, the silicon which remains in the cup may be measured using a bench-top spectrometer. However, this method may be laborious and time-consuming and not applicable to real-time field measurements of contaminants on surface coatings.

Therefore, a method for determining surface contamination of materials using non-destructive Mid-IR spectroscopy which enables real-time field measurement of contamination on coatings and non-metallic substrates (composites) in manufacturing and repair situations is needed.

SUMMARY

The disclosure is generally directed to a method of determining contamination on a material having suspected contamination. An illustrative embodiment of the method includes irradiating the material having suspected contamination with infrared energy over a spectrum of wavelengths; detecting the infrared energy reflected from the material having suspected contamination over the spectrum of wavelengths; performing multivariate analysis on the spectrum of the reflected infrared energy; comparing results of the multivariate analysis with a predetermined calibration of infrared energy spectra comprising the spectrum of wavelengths collected from at least one reference material; and determining presence or absence of contamination on the material having suspected contamination based on the predetermined calibration.

In some embodiments, the method of determining contamination on a material having suspected contamination may include irradiating the material having suspected contamination with infrared energy over a spectrum of wavelengths between about 400 and about 4000 wavenumbers ($cm^{-1}$); detecting the infrared energy reflected from the material having suspected contamination over the spectrum of wavelengths; performing multivariate analysis on the spectrum of the reflected infrared energy; comparing results of the multivariate analysis with a predetermined calibration of infrared energy spectra comprising the spectrum of wavelengths collected from at least one reference material; and determining presence or absence of contamination on the material having suspected contamination based on the predetermined calibration.

In some embodiments, the method of determining contamination on a material coating having suspected contamination on a substrate may include irradiating the material coating having suspected contamination with infrared energy over a spectrum of wavelengths between about 650 and about 4000 wavenumbers ($cm^{-1}$); detecting the infrared energy reflected from the material coating having suspected contamination over the spectrum of wavelengths; performing multivariate analysis on the spectrum of the reflected infrared energy; comparing results of the multivariate analysis with a predetermined calibration of infrared energy spectra comprising the spectrum of wavelengths collected from at least one reference material coating; and determining presence or absence of contamination on the material coating having suspected contamination based on the predetermined calibration using a hand-held IR spectrometer.

BRIEF DESCRIPTION OF THE ILLUSTRATIONS

DETAILED DESCRIPTION OF THE PREFERRED EMBODIMENT

The present disclosure is generally directed to a method of non-destructively measuring or determining the presence of contaminants on a material coating on a substrate. The method may be accomplished by making an infrared (IR) spectroscopy measurement with an IR spectrometer over a spectrum of wavelengths in the mid-IR, such as with a portable mid-IR spectrometer, for example and without limitation. Multivariate calibration of mid-IR spectra to at least one "clean" or uncontaminated reference material may be performed in order to determine the presence of contaminants on the material coating.

It will be appreciated that although the disclosure is particularly explained with reference to using IR spectroscopy to measure contaminants on a material coating on a substrate (including metallic or non-metallic surfaces on substrates) used in portions of aircraft, the disclosure may additionally be advantageously used to measure contaminants on a material coating on surfaces in general. The method may facilitate field measurement of contamination on coatings and non-metallic surfaces in manufacturing and repair situations using real-time measurement in a process line.

Either a portable or non-portable IR spectrometer may be used to carry out the mid-IR spectroscopy measurements according to the present disclosure. The spectrum of wavelengths used to make the mid-IR spectroscopy measurements may include all or a portion of the wavelengths between about 400 and about 4000 wavenumbers ($cm^{-1}$) (25 to 2.5 microns) more preferably between about 650 and about 4000 wavenumbers ($cm^{-1}$) (15.4 to 2.5 microns). In some embodiments, a hand-held portable spectrometer capable of performing Fourier Transform IR (FT-IR) spectroscopy measurements over the mid-IR range of wavelengths outlined above may be used to perform the IR spectroscopy measurements according to the present disclosure.

The hand-held portable FT-IR spectrometer may have the capability to supply source IR energy to a sample at a predetermined incident angle between about 30 to about 60 degrees, and collect reflected light from the sample through a broad range of angles which may exclude the incident angle. The hand-held portable IR device may have the ability to make diffuse reflectance IR spectroscopic measurements (also referred to as an external reflectance IR spectroscopic measurement). NOTE: the new non-contact system disclosed herein has similar geometry and capability.

Figure 1:
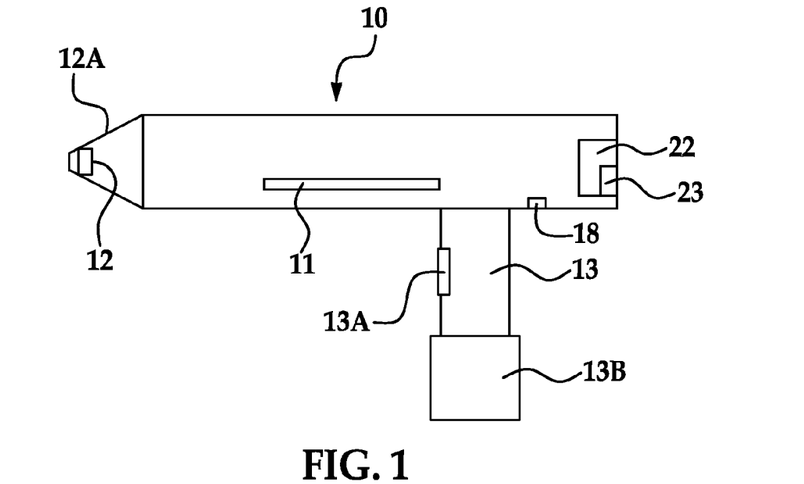
FIG. 1 is a schematic diagram of an exemplary hand-held portable mid-IR spectrometer suitably used to make mid-IR spectroscopy measurements according to an embodiment of the method.

Referring to FIG. 1, a side view of a portable (handheld) IR spectrometer 10 which is suitable for implementation of an illustrative embodiment of the disclosure. The portable IR spectrometer 10 may have the capability of performing near-IR and/or mid-IR spectroscopy measurements, and in some embodiments may at least have the capability of performing mid-IR (FT-IR) spectroscopy measurements. As used herein, the term 'hand-held portable' means an instrument that may be easily carried and picked up and move about to make IR spectroscopy measurements by an average person, e.g., has a weight of less than about 8 pounds and may be hand-held and aimed (or held against) a location on the measurement surface to make a spot-size measurement. An example of an IR spectrometer which is suitable for implementation of the disclosure is the EXOSCAN (trademark) hand-held FT-IR spectrometer which can be obtained from A2 Technologies of Danbury, Conn. The non-contact device is called a LaserScan and is made by Block Engineering in Marlborough, Mass.

The portable IR spectrometer 10 may also include a microprocessor and memory (e.g. micro-processor board 11) and may be interfaced (placed in communication with) with other computing devices (e.g., USB port 18). The portable IR spectrometer 10 may be supplied power by one or more batteries (e.g., 13B in handle portion 13 or other portion of IR spectrometer 10). The portable IR spectrometer 10 may be programmable and/or capable of accepting, storing, and executing preprogrammed instructions for carrying out IR spectroscopy measurements. The portable IR spectrometer 10 may have the capability to emit incident IR light (energy) 34 (FIGS. 2 and 3) and collect reflected mid-IR spectra 35 over all or portions of an operating wavelength range (e.g., 400 wavenumbers ($cm^{-1}$) to about 4000 wavenumbers ($cm^{-1}$)) and to store the spectra and perform mathematical manipulation of the data comprising the spectra including performing multivariate analysis of the spectra.

In some embodiments, the portable IR spectrometer 10 may have an elongated front portion 12A which contains an one or more IR transparent energy windows e.g., 12, for example the front portion 12A may have a nose-like or snout-like (probe) shape, which may advantageously aid in the aiming and positioning of the portable IR spectrometer 10 with respect to a measurement surface to make a spot size IR spectroscopy measurement of a pre-defined size. For example, an IR-transparent window 12 may be set back from the surface of the nose portion 12A, which may be placed on or close to the surface of the sample to be measured to produce a known spot-size measurement area, e.g., which may be any size but preferably ranges from an area of about 1 $mm^2$ to about 1 $cm^2$. In some embodiments, the nose portion 12A may be an interchangeable IR probe, including different IR spectrum ranges and/or measurement spot sizes, and may include IR transparent fiber optics.

The portable IR spectrometer 10 may include a triggering device e.g. 13A on handle portion 13 for triggering an IR spectroscopy or the IR spectroscopy measurement may be alternately triggered e.g., by softkeys on an interactive LCD touchscreen 22. The touchscreen 22 may further include a display 23 which displays the reflected mid-IR spectra 35. It will be appreciated that the portable IR spectrometer 10 may be of any suitable ergonomic shape to enhance the portability and ease of holding and manipulating the spectrometer to carryout hand-held IR spectroscopy measurements.

The portable IR spectrometer 10 may have the ability to store collected IR spectra and perform mathematical manipulation of the data comprising the spectra including multivariate analysis of the spectra. The portable IR spectrometer 10 may include interactive buttons and/or softkeys e.g., on the interactive LCD or LED touchscreen 22, or elsewhere, and may include a textual presentation on the display 23 to guide the operator through an IR spectroscopy measurement process.

In addition, suitable calibration background reference standard materials and wavelength reference standard materials may be provided for calibrating the IR spectrometer 10 prior to performing IR spectroscopy measurements according to embodiments of the disclosure.

In some embodiments, an IR spectrometer used to carry out an IR spectroscopy measurement according to the present invention, such as the portable IR spectrometer 10, may be provided and have stored in memory one or more calibration algorithms for IR spectra for use in a subsequent IR spectroscopy measurement and multivariate prediction processes where the IR spectra to be predicted is made with respect to material in a similar condition to an area of the sample with a known level (e.g. baseline including the absence of), the property to be measured, such as the absence of a bond primer film coating on a roughened metallic substrate. For example, it has been found that wavelengths in the mid-IR range, as noted above, are particularly useful for determining the presence of contaminants such as silicon which can affect the adhesion of subsequent coatings including TEFLON (trademark) release agents, oils and greases, for example and without limitation, on an organic material such as bond primer on a metallic surface, including a roughened metallic surface, or on a non-metallic surface.

In addition, a previously determined multivariate calibration of IR spectra versus thickness of a film coating may be stored in memory within the IR spectrometer. For example, the predetermined calibration may be determined by calibrating to a plurality of model IR spectra (absorbance and/or reflectance at multiple wavelengths) with a known level of contaminants on model bond primer film coatings from a respective plurality of model samples where the known level of contaminants for each of the model samples is determined by separate and independent measurements, e.g., optical or electron microscopy.

As such, an IR spectrometer, such as portable IR spectrometer 10, may be calibrated such that an in-situ (real-time) analysis of collected IR spectra taken from an actual sample may be performed to determine the presence of contaminants on the film coating. For example, the calibration may be done on an external computer and the resulting calibration model may be down-loaded to the hand-held mid-IR system. Preferably, a quantified (numerical) level of the level of contamination may be determined in real-time by a portable IR spectrometer, such as the IR spectrometer 10, and stored and/or output. Additionally or alternatively, a pass/fail type determination (level of contamination above or below a threshold numerical value) and resulting indication thereof may stored and/or output.

The portable IR spectrometer 10, or another IR spectrometer used to carry out IR spectroscopy measurements according to embodiments of the disclosure, may include a computer processor capable of multivariate analysis of the IR spectra or the calibration may be done on an external computer (controller) and the resulting calibration model downloaded to the hand-held mid-IR system. For example and without limitation, the IR spectrometer (or an associated computer/controller) may have the ability to mathematically and statistically correlate and determine changes in a plurality of variables (e.g., IR spectra including reflectance at a plurality of wavelengths) with respect to one or more reference IR spectra.

There are many suitable multivariate techniques that may be used to make an IR spectroscopy measurement according to the present invention including, but not limited to, quantification methodologies, such as, partial least squares, principal component regression ("PCR"), linear regression, multiple linear regression, stepwise linear regression, ridge regression, radial basis functions, and the like.

In addition, suitable multivariate statistical approaches may include classification methodologies, such as, linear discriminant analysis ("LDA"), cluster analysis (e.g., k-means, C-means, etc., both fuzzy and hard), and neural network ("NN") analysis.

Further, it will be appreciated that there are several data processing methods that may be suitably used in connection with suitable multivariate statistical approaches including smoothing, taking first and second derivatives of the IR spectra, and peak enhancement methods.

In addition, multivariate analysis of collected IR spectra may include the selection and clustering together of groups of wavelengths on which to perform a regression analysis to determine a corresponding change in the IR spectra (spectrum) (e.g., reflectance) with respect to reference spectra (spectrum). It will be appreciated that an individual IR spectrum may be formed from several IR spectra (e.g., by averaging techniques known in the art). In addition, the raw IR spectra may transformed into second IR spectra by taking first and/or second derivatives and performing smoothing and/or peak enhancement as well as carrying out regression analysis. For example and without limitation, manipulation of the raw IR spectra by smoothing algorithms prior to or following taking a first derivative and then quantifying a degree of change of the IR spectra from a reference spectrum (similarly processed) according to a regression or partial lest squares analysis may be performed.

In addition, the IR spectroscopy measurement process may include collecting reference IR spectra (including calculated absorbance and/or reflectance) which may serve as a baseline from which to determine relative changes in sample IR spectra by multivariate analysis. In addition, various processing methods as are known in the art may be used to form a single IR spectrum from a collection of a plurality of collected IR spectra, including various averaging techniques, for example to improve a signal to noise ratio, prior to carrying out multivariate analysis to determine a change from reference spectrum. It will be appreciated that the change may include a change at one or more wavelengths including clusters of wavelengths.

Figure 2:
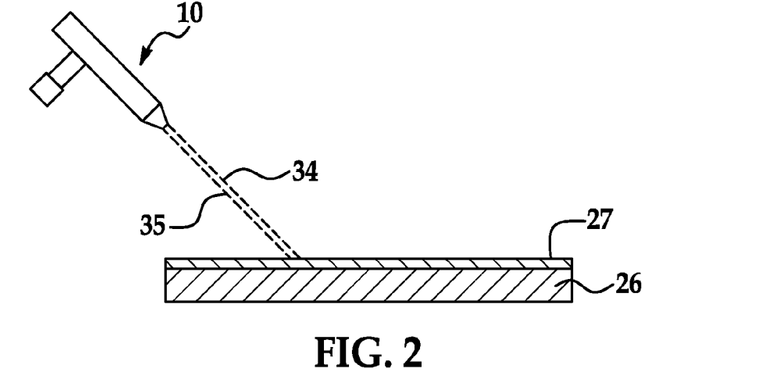
FIG. 2 illustrates irradiation of a reference material with mid-IR radiation according to an embodiment of the method.

Referring to FIG. 2, irradiation of a reference material 27 on a substrate 26 with an incident mid-IR beam 34 is shown according to a method of the disclosure is shown. In some embodiments, the substrate 26 may be a metallic substrate. In some embodiments, the substrate 26 may be a non-metallic substrate. The reference material 27 may be an organic material such as a primer or coating on the substrate 26. The reference material 27 may be "clean" or devoid of contaminants which may adversely affect the adhesion of subsequent coatings including but not limited to TEFLON (trademark) release agents, oils and greases. In some applications, the reference material 27 may be substantially devoid of silicon contaminant.

An incident mid-IR beam 34 may be emitted from the IR spectrometer 10 against the reference material 27. The mid-IR beam 34 may include all or a portion of the wavelengths between about 400 and about 4000 wavenumbers ($cm^{-1}$) (25 to 2.5 microns) more preferably between about 650 and about 4000 wavenumbers ($cm^{-1}$) (15.4 to 2.5 microns). The incident mid-IR beam 34 may strike the reference material 27 at a predetermined incident angle between about 30 to about 60 degrees. A reflected mid-IR spectra 35 may be reflected from the reference material 27 back to the IR spectrometer 10 through a broad range of angles which may exclude the incident angle. The mid-IR spectra 35 which are reflected from the reference material 27 may be stored in the microprocessor and memory 11 (FIG. 1) of the IR spectrometer 10. In some applications, multiple mid-IR spectra 35 may be collected from multiple reference materials 27 and stored in the microprocessor and memory 11.

Figure 3:
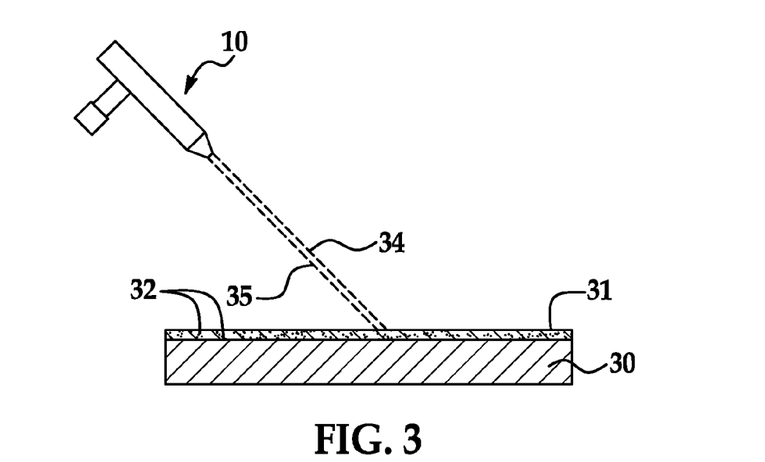
FIG. 3 illustrates irradiation of a material having suspected contamination with mid-IR radiation according to an embodiment of the method.

Referring to FIG. 3, irradiation of a material having suspected contamination 31 on a substrate 30 with an incident mid-IR beam 34 is shown according to a method of the disclosure is shown. In some embodiments, the substrate 30 may be a metallic substrate. In some embodiments, the substrate 30 may be a non-metallic substrate. The material having suspected contamination 31 may be an organic material such as a primer or coating on the substrate 30. Contaminants 32 in the material having suspected contamination 31 may adversely affect the adhesion of subsequent coatings including but not limited to TEFLON (trademark) release agents, oils and greases. In some applications, the contaminants 32 in the material having suspected contamination 31 may be substantially devoid of silicon contaminant.

An incident mid-IR beam 34 may be emitted from the IR spectrometer 10 against the material having suspected contamination 31. The mid-IR beam 34 may include all or a portion of the wavelengths between about 400 and about 4000 wavenumbers (cm$^{-1}$) (25 to 2.5 microns) more preferably between about 650 and about 4000 wavenumbers (cm$^{-1}$) (15.4 to 2.5 microns). The incident mid-IR beam 34 may strike the material having suspected contamination 31 at a predetermined incident angle between about 30 to about 60 degrees. A reflected mid-IR spectra 35 may be reflected from the material having suspected contamination 31 back to the IR spectrometer 10 through a broad range of angles which may exclude the incident angle. The mid-IR spectra 35 which are reflected from the material having suspected contamination 31 may be stored in the microprocessor and memory 11 (FIG. 1) of the IR spectrometer 10.

Multi-variant analysis may be used to compare the IR spectra which were obtained by irradiation of the material having suspected contamination 31 with the IR spectra which were obtained by irradiation of the reference material or materials 27. An output may be displayed on the display 23 of the IR spectrometer 10. The output may indicate the presence of contaminants on the material having suspected contamination 31 if the spectrum which was obtained by irradiation of the material having suspected contamination 31 has characteristics which differ from the spectrum which was obtained by irradiation of the reference material or materials 27.

Figure 4:
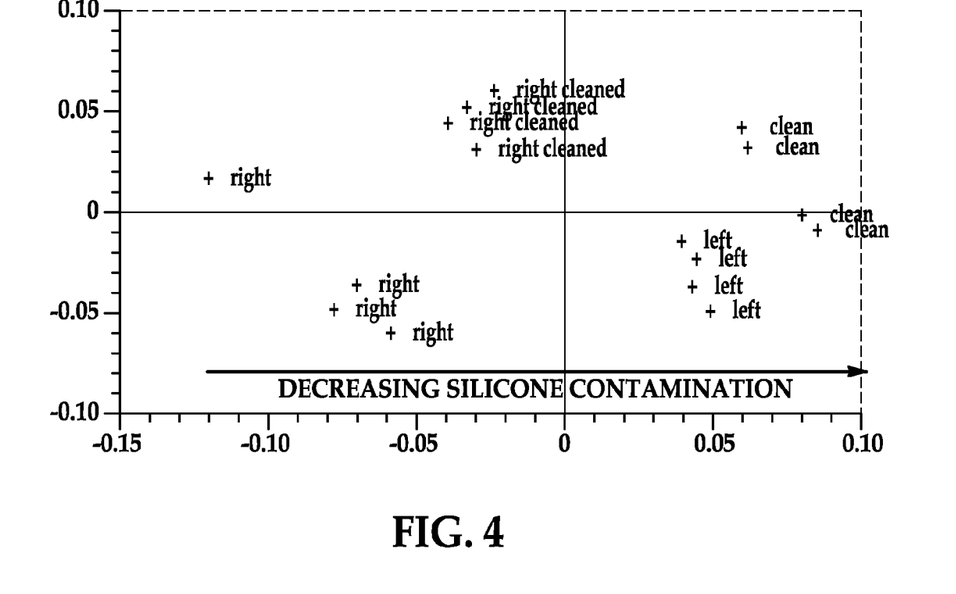
FIG. 4 is a graph showing the sample "scores" plot for IR measurement of a series of silicone contaminated and clean epoxy primer surfaces. Those label "right" have the most silicone contamination, "right cleaned" has less contamination, "left" has very little silicone contamination, and "clean" has no silicone contamination. Notice the progression of most silicone to least silicone from left to right on the plot.

FIG. 4 is a graph showing the sample "scores" plot for IR measurement of a series of silicone contaminated and clean epoxy primer surfaces. Those label "right" have the most silicone contamination, "right cleaned" has less contamination, "left" has very little silicone contamination, and "clean" has no silicone contamination. Notice the progression of most silicone to least silicone from left to right on the plot. FIG. 4 illustrates data for various degrees of silicone contamination.

Figure 5:
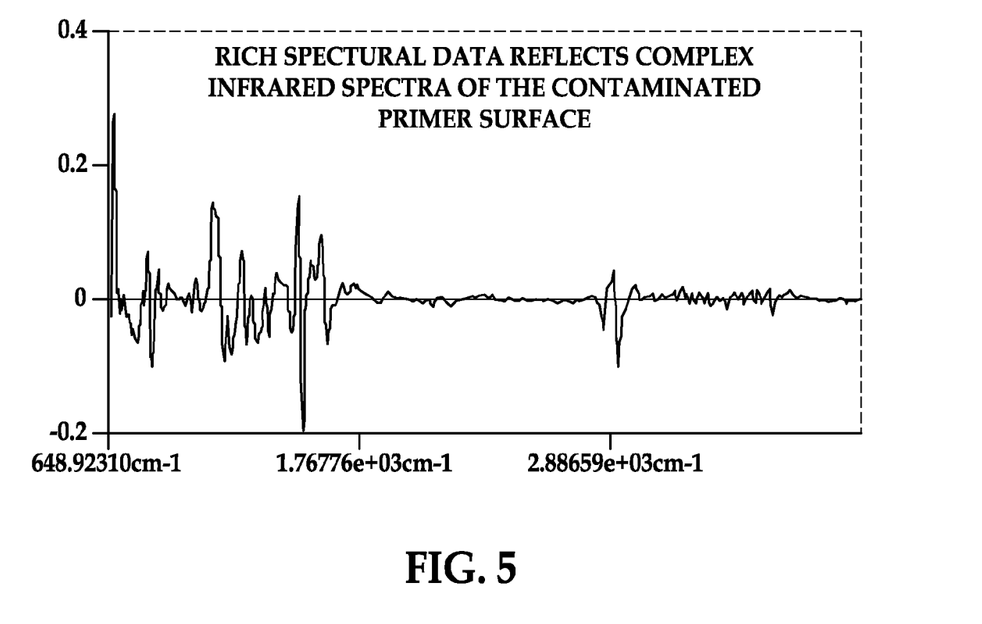
FIG. 5 is a graph showing the IR spectrum wavelength space that allows separation of silicone contamination levels. The larger the peaks the more useful they are for the contamination measurement.

FIG. 5 is a graph showing the IR spectrum wavelength space that allows separation of silicone contamination levels. The larger the peaks the more useful they are for the contamination measurement. FIG. 5 illustrates the IR spectrum wavelength space that allows separation of silicon contamination levels.

Figure 6:
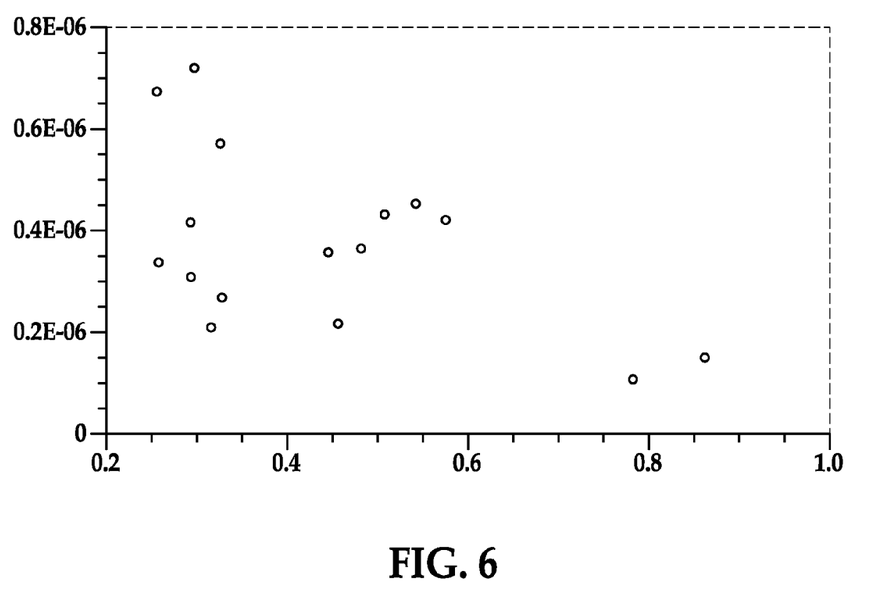
FIG. 6 is a graph showing residual variance versus model leverage for the measurements in this example. This plot shows there are no significant outliers in the analysis.

FIG. 6 is a graph showing residual variance versus model leverage for the measurements in this example. This plot shows there are no significant outliers in the analysis. FIG. 6 illustrates a sample residual variance versus model leverage plot.

Figure 7:
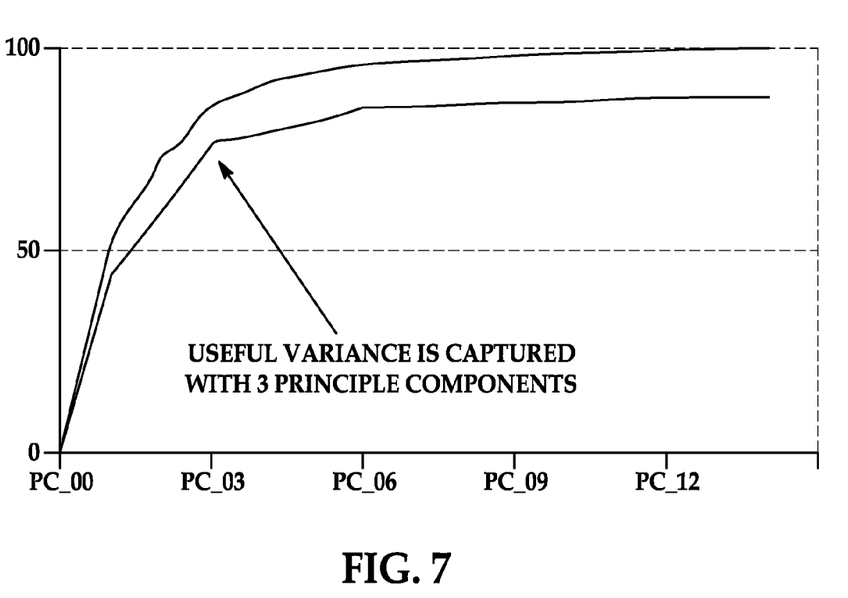
FIG. 7 is a graph showing the variance captured by this contamination analysis model. Most useful variance in the spectral data is captured by 3 principle components which usually suggests a robust model.

FIG. 7 is a graph showing the variance captured by this contamination analysis model. Most useful variance in the spectral data is captured by 3 principle components which usually suggests a robust model. FIG. 7 illustrates the variance captured by the contamination analysis model.

Figure 8:
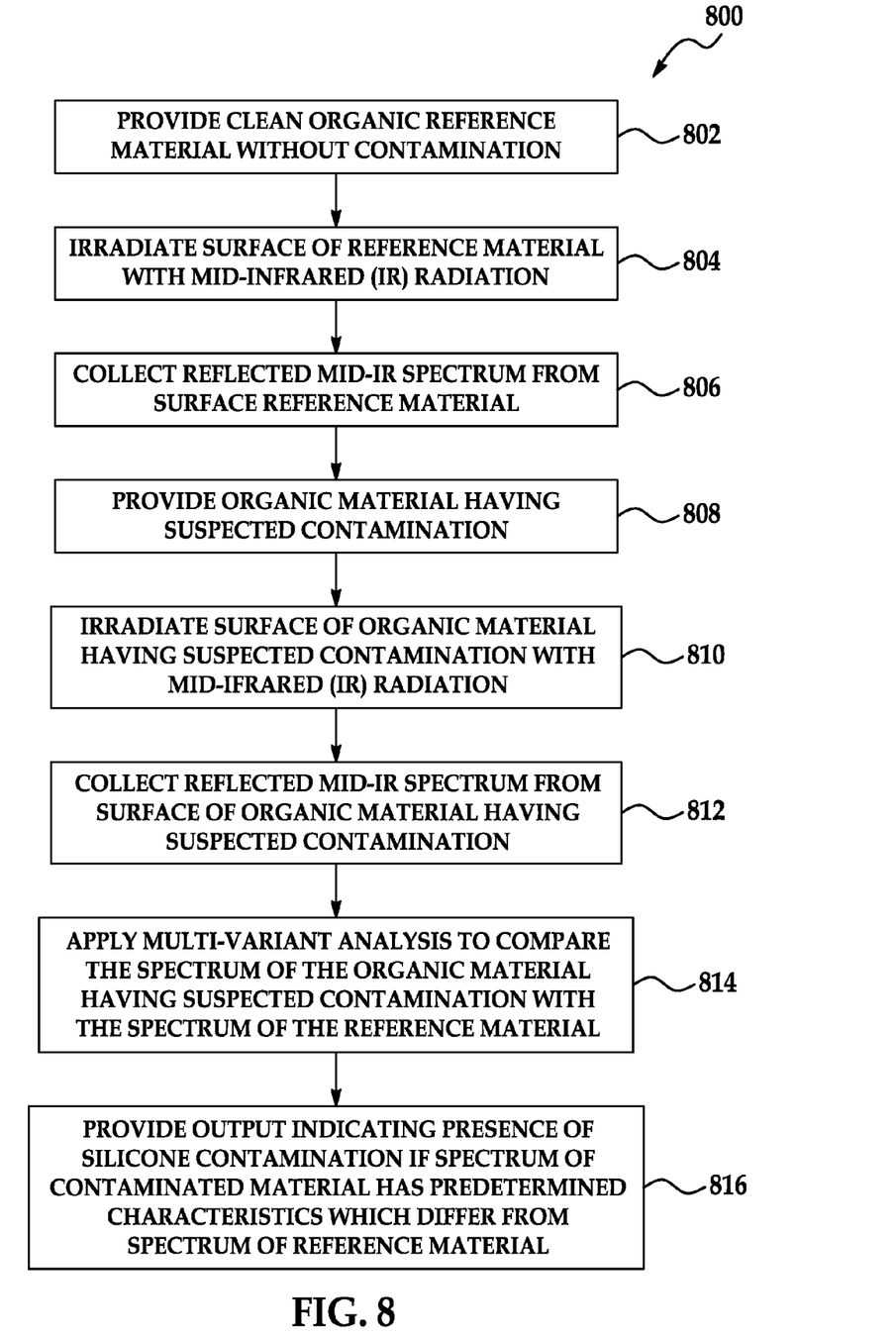
FIG. 8 is a flow diagram according to an embodiment of the method.

Referring to FIG. 8, a flow diagram 800 according to an embodiment of the method for determining contamination of a material using mid-IR spectroscopy is shown. In block 802, at least one sample of a clean or uncontaminated organic reference material may be provided. In block 804, the surface of the reference material may be irradiated with mid-IR radiation. In block 806, the mid-IR spectrum which is reflected from the surface of the reference material may be collected. In block 808, an organic material having suspected contamination may be provided. In block 810, the surface of the organic material having suspected contamination may be irradiated with mid-IR radiation. In block 812, the mid-IR spectrum which is reflected from the surface of the organic material having suspected contamination may be collected. In block 814, multi-variant analysis may be used to compare the spectrum obtained by irradiation of the organic material having suspected contamination with the spectrum obtained by irradiation of the reference material. In block 816, an output may indicate the presence of a contaminant such as silicon on the surface of the material having suspected contamination if the spectrum obtained from the surface of the material having suspected contamination has predetermined characteristics which differ from the spectrum which was obtained from the reference material.

Figure 9:
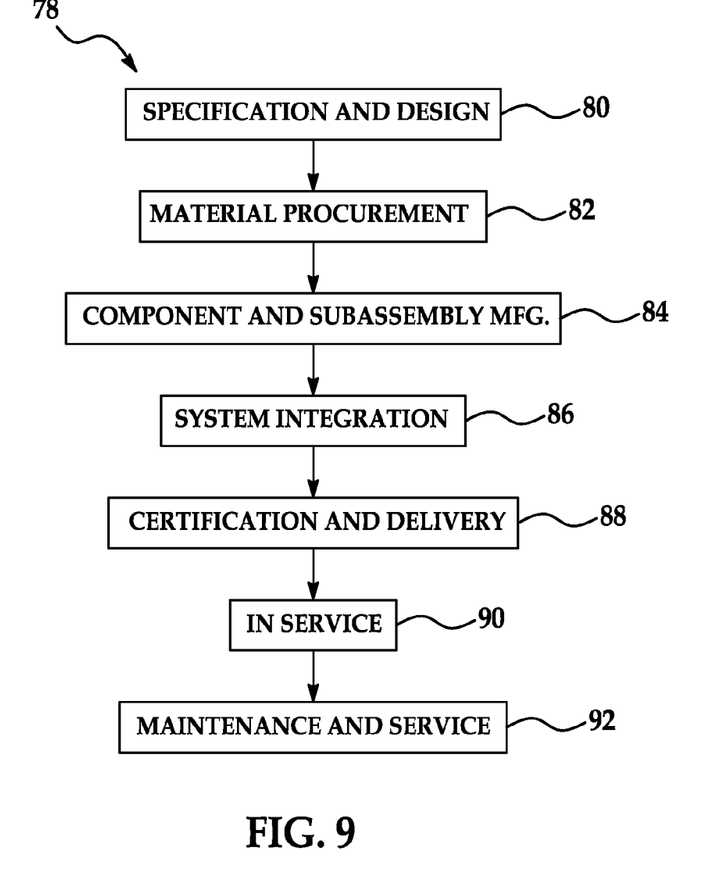
FIG. 9 is a flow diagram of an aircraft and service methodology.
Figure 10:
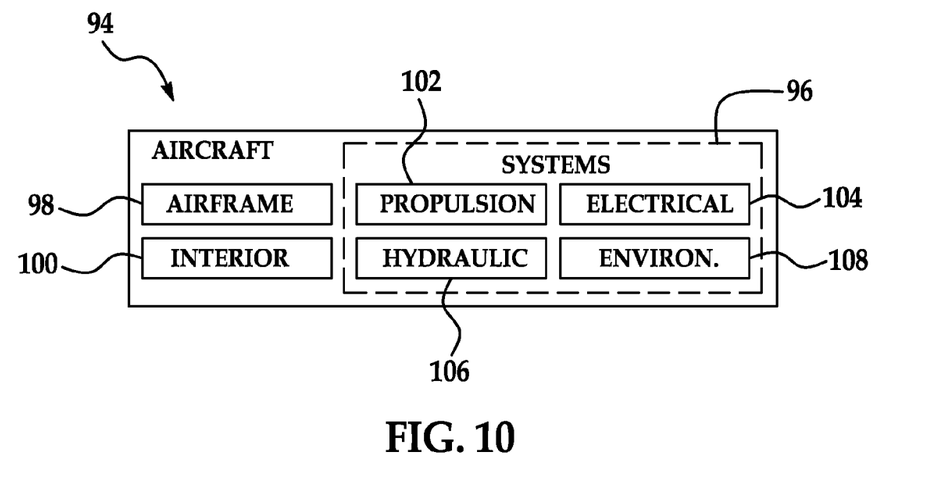
FIG. 10 is a block diagram of an aircraft.

Referring next to FIGS. 9 and 10, embodiments of the disclosure may be used in the context of an aircraft manufacturing and service method 78 as shown in FIG. 9 and an aircraft 94 as shown in FIG. 10. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 10, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of determining contamination on a coating or a non-metallic material having suspected contamination, comprising:

irradiating a reference coating or a non-metallic material with infrared energy over a spectrum of wavelengths using a spectrometer;

detecting first infrared energy reflected from said reference coating or non-metallic material over said spectrum of wavelengths;

irradiating said coating or non-metallic material having suspected contamination with infrared energy over a spectrum of wavelengths using the spectrometer or another spectrometer, said reference coating or non-metallic material being associated with said coating or non-metallic material having suspected contamination;

detecting second infrared energy reflected from said coating or non-metallic material having suspected contamination over said spectrum of wavelengths;

performing multivariate analysis on said first and second reflected infrared energy;

comparing results of said multivariate analysis with calibration information for infrared energy spectra comprising said spectrum of wavelengths associated with said reference coating or non-metallic material; and determining presence or absence of contamination on said material having suspected contamination based on said calibration information.

2. The method of claim 1 wherein said material comprises an organic material.

3. The method of claim 1 further comprising a substrate and wherein said material having suspected contamination comprises a coating on said substrate.

4. The method of claim 3 wherein said substrate comprises a metallic substrate.

5. The method of claim 3 wherein said substrate comprises a non-metallic substrate.

6. The method of claim 3 wherein said coating comprises a bonding primer on said substrate.

7. The method of claim 1 wherein said determining presence or absence of contamination on said material having suspected contamination comprises determining presence or absence of silicon contamination on said material having suspected contamination.

8. The method of claim 1 wherein said irradiating said material having suspected contamination with infrared energy over a spectrum of wavelengths comprises irradiating said material having suspected contamination with infrared energy over a spectrum of wavelengths using a hand-held IR spectrometer.

9. A method of determining contamination on a coating or a non-metallic material having suspected contamination, comprising:

irradiating said coating or non-metallic material having suspected contamination with infrared energy over a spectrum of wavelengths;

detecting said infrared energy reflected from said coating or a non-metallic material having suspected contamination over said spectrum of wavelengths;

performing multivariate analysis on the spectrum of said reflected infrared energy;

comparing results of said multivariate analysis with calibration information for infrared energy spectra comprising said spectrum of wavelengths associated with a reference material; and determining presence or absence of contamination on said material having suspected contamination based on said calibration information.

10. The method of claim 9 wherein said material comprises an organic material.

11. The method of claim 9 further comprising a substrate and wherein said material having suspected contamination comprises a coating on said substrate.

12. The method of claim 11 wherein said substrate comprises a metallic substrate.

13. The method of claim 11 wherein said substrate comprises a non-metallic substrate.

14. The method of claim 11 wherein said coating comprises a bonding primer on said substrate.

15. The method of claim 9 wherein said determining presence or absence of contamination on said material having suspected contamination comprises determining presence or absence of silicon contamination on said material having suspected contamination.

16. The method of claim 9 wherein said irradiating said material having suspected contamination with infrared energy over a spectrum of wavelengths comprises irradiating said material having suspected contamination with infrared energy over a spectrum of wavelengths using a hand-held IR spectrometer.

17. A method of determining contamination on a material coating having suspected contamination on a substrate, comprising:

irradiating said material coating having suspected contamination with infrared energy over a spectrum of wavelengths;

detecting said infrared energy reflected from said material coating having suspected contamination over said spectrum of wavelengths;

performing multivariate analysis on the spectrum of said reflected infrared energy;

comparing results of said multivariate analysis with a predetermined calibration of infrared energy spectra comprising said spectrum of wavelengths collected from at least one reference material coating; and, determining presence or absence of contamination on said material coating having suspected contamination based on said predetermined calibration using a hand-held infrared spectrometer.

18. The method of claim 17 wherein said substrate comprises a metallic substrate.

19. The method of claim 17 wherein said substrate comprises a non-metallic substrate.

20. The method of claim 17 wherein said coating comprises a bonding primer on said substrate and said determining presence or absence of contamination on said material having suspected contamination comprises determining presence or absence of silicon contamination on said bonding primer.

* * * * *